(12) United States Patent
Matthis et al.

(10) Patent No.: US 8,641,737 B2
(45) Date of Patent: Feb. 4, 2014

(54) BONE ANCHORING DEVICE (75) Inventors: Wilfried Matthis, Weisweil (DE); Lutz Biedermann, VS-Villingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1647 days.

(21) Appl. No.: 11/697,220

(22) Filed: Apr. 5, 2007

(65) Prior Publication Data

US 2007/0265621 A1 Nov. 15, 2007

Related U.S. Application Data (60) Provisional application No. 60/790,084, filed on Apr. 6, 2006.

(30) Foreign Application Priority Data

Apr. 6, 2006 (EP) ..................................... 06007324

(51) Int. Cl.
*A61B 17/70* (2006.01)
(52) U.S. Cl.
USPC .......................................... 606/265; 606/266
(58) Field of Classification Search
USPC .............................. 606/60, 246–279, 300–320
See application file for complete search history.

(56) References Cited

U.S. PATENT DOCUMENTS

| | | | |
|---|---|---|---|
| 5,776,135 A * | 7/1998 | Errico et al. | 606/266 |
| 6,063,089 A * | 5/2000 | Errico et al. | 606/278 |
| 6,443,953 B1 | 9/2002 | Perra et al. | |
| 6,520,963 B1 * | 2/2003 | McKinley | 606/266 |
| 6,676,661 B1 * | 1/2004 | Benlloch et al. | 606/264 |
| 6,736,820 B2 | 5/2004 | Biedermann et al. | |
| 6,981,973 B2 * | 1/2006 | McKinley | 606/264 |
| 8,052,726 B2 * | 11/2011 | Nayet et al. | 606/278 |
| 2003/0032957 A1 * | 2/2003 | McKinley | 606/61 |
| 2003/0055426 A1 | 3/2003 | Carbone et al. | |

(Continued)

FOREIGN PATENT DOCUMENTS

| | | |
|---|---|---|
| TW | M285330 | 1/2006 |
| WO | WO 2007/095428 A1 | 8/2007 |

OTHER PUBLICATIONS

International Search Report, dated Sep. 18, 2006, Application No. EP 06007324, Date of Completion of Search Sep. 7, 2006, Place of Search Munich (5 pages).

*Primary Examiner* — Pedro Philogene
*Assistant Examiner* — Lynnsy Schneider
(74) *Attorney, Agent, or Firm* — Christie, Parker & Hale, LLP (57) ABSTRACT

A bone anchoring device includes a bone anchoring element having a shaft to be anchored in the bone and a head, a receiving part for receiving a rod to be connected to the bone anchoring element, and a pressure member acting onto the head to lock the position of the head relative to the receiving part, the receiving part is formed in one piece and includes an open first bore with a first bore axis, a recess shaped and sized to receive a rod having a longitudinal axis, and a second bore having a second bore axis. The second bore is in communication with the first bore and is sized to receive the head with a part of the shaft extending through the second bore. The second bore axis includes an angle of approximately 90° with a plane defined by the first bore axis and the longitudinal axis of the rod.

20 Claims, 6 Drawing Sheets

(56) References Cited

U.S. PATENT DOCUMENTS

| | | |
|---|---|---|
| 2003/0167058 A1 | 9/2003 | Shluzas |
| 2004/0210216 A1* | 10/2004 | Farris et al. .................... 606/61 |
| 2005/0154391 A1 | 7/2005 | Doherty et al. |
| 2005/0154393 A1* | 7/2005 | Doherty et al. ................. 606/73 |
| 2005/0159750 A1* | 7/2005 | Doherty .......................... 606/73 |
| 2005/0187548 A1* | 8/2005 | Butler et al. .................... 606/61 |
| 2006/0116677 A1* | 6/2006 | Burd et al. ...................... 606/61 |
| 2006/0149240 A1* | 7/2006 | Jackson .......................... 606/61 |
| 2007/0083206 A1 | 4/2007 | Du |
| 2007/0233067 A1* | 10/2007 | Taylor ............................. 606/61 |

\* cited by examiner

BONE ANCHORING DEVICE

CROSS-REFERENCE TO RELATED APPLICATION(S)

The present application claims the benefit of U.S. Provisional Patent Application Ser. No. 60/790,084, filed Apr. 6, 2006, and claims priority from European Patent Application EP06007324.4, filed Apr. 6, 2006, the entire disclosures of which are incorporated herein by reference.

BACKGROUND

The invention relates to a bone anchoring device in particular to a bone anchoring device which can be used for stabilization of the spine in the sacro-iliac region.

Stabilization of the spine in the sacro-iliac region requires in certain constellations that the bone screw which is to be connected with the spinal stabilization rod is screwed laterally into the bone.

U.S. Pat. No. 6,981,973 discloses a low profile vertebral alignment/fixation assembly which comprises a hemispherical headed pedicel screw disposed within a slotted coupling unit designed to allow angular adjustment of the pedicle screw up to 90° and which may be locked into position via a single internal locking nut once a rod has been inserted into the slotted coupling unit. The nut has an engagement portion designed to engage the rod. The head of the screw is locked by the action of the rod pressing onto the head. The assembly can be anchored in the ileum bone with the screw aligned at a 90° angle with reference to the coupling unit.

US 2005/0159750 A1 discloses a bone anchor assembly comprising a bone anchor and a receiving member for receiving a spinal rod. The bone anchor can be adjusted in the receiving member such that the longitudinal axis of the bone anchor is at an angle of 0° to 90° relative to the receiving member in a plane which contains the longitudinal axis of the spinal rod. A main application of this anchor assembly is the stabilization of the cervical spine where it can be necessary to pivot the bone anchors out of an alignment to avoid interference due to their close proximity.

US 2005/0154391 A1 discloses a bone anchor assembly comprising a bone anchor and a receiving member to receive a spinal rod. The receiving member has a first section and a second section which is coupled to the bone anchor. The second section is movably connected to the first section. The bone anchor may be adjusted such that the longitudinal axis of the bone anchor is at an angle of 0° to 90° relative to the receiver member.

U.S. Pat. No. 6,736,820 discloses a bone screw having a screw member with a threaded section and a head and a receiving part for receiving a rod to be connected to the bone screw. The receiving part has an open first bore and a substantially U-shaped cross-section to receive the rod and a second bore on the opposite end with a seat for the head. In order that the screw member can be pivoted to at least one side by an enlarged angle, the edge bounding the free end of the second bore is of asymmetric construction.

US 2003/0055426 A1 discloses a biased angulation bone fixation assembly including and anchoring element and a coupling element having a first bore coaxial with a first longitudinal axis and a second bore coaxial with a second longitudinal axis wherein said first and second longitudinal axes are transverse to one another. The coupling element also includes rod receiving openings for receiving a spinal rod.

Based on the above, there is a need to provide an improved bone anchoring device which allows a lateral fixation of the bone anchoring element in the bone, e.g., at an angle of at least 90° relative to the receiving part in a plane perpendicular to the longitudinal axis of the spinal rod which is suitable for use in the sacro-iliac region of the spine.

SUMMARY

The bone anchoring element of the disclosed bone anchoring device is compact with few parts and provides a reliable fixation.

The bottom of the receiver part and the surface of the pressure element which contacts the head of the bone anchoring element preferably have a spherical surface which correspond to the spherical section of the surface of the head. This provides for a balanced clamping stress to clamp the head. As a result, the clamping stress onto the head can be reduced.

The bone anchoring device has a further advantage in that it allows to orient the screw relative to the receiving part at an angle which is greater than 90°.

Further features and advantages of the invention will become apparent and will be best understood by reference to the following detailed description of embodiments taken in conjunction with the accompanying drawings.

DETAILED DESCRIPTION

Figure 1:
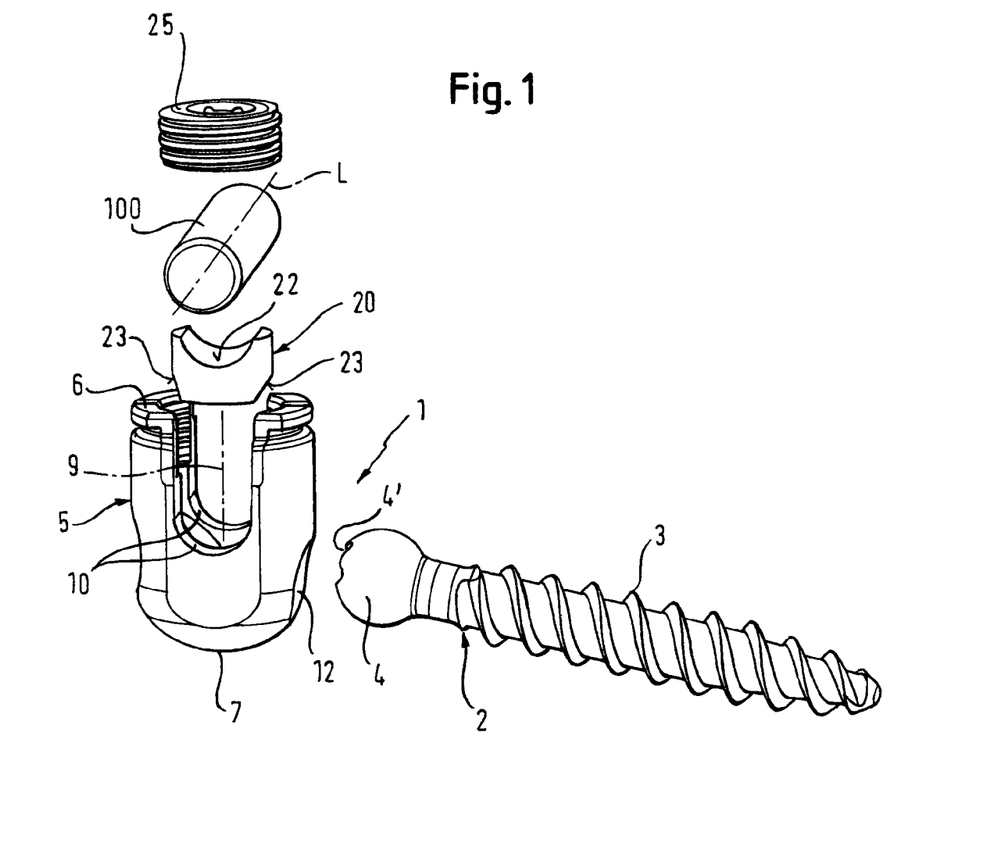
FIG. 1 shows an exploded perspective view of a first embodiment of the bone anchoring device.
Figure 2:
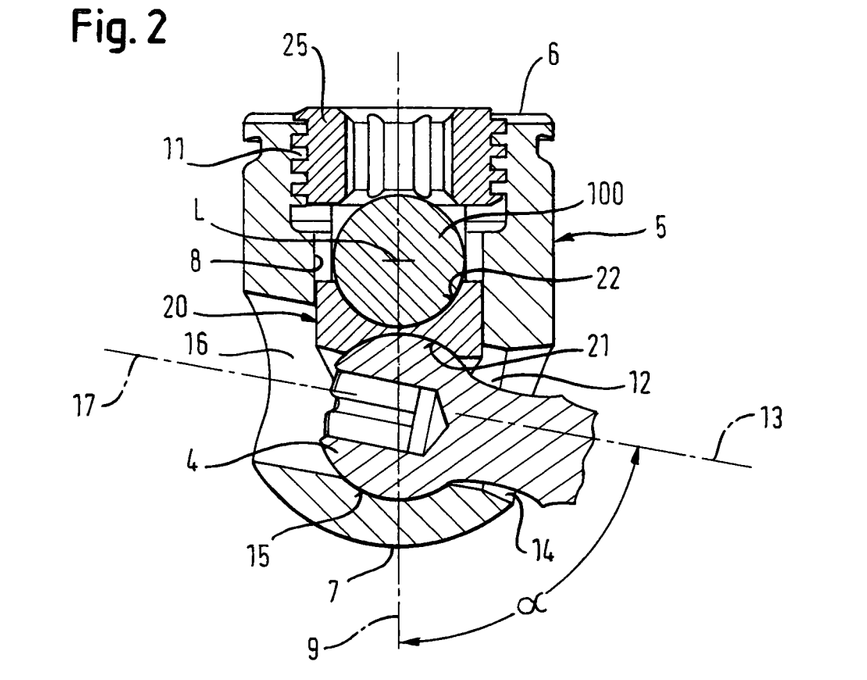
FIG. 2 shows a sectional view of the bone anchoring device of FIG. 1 in an assembled state.
Figure 3:
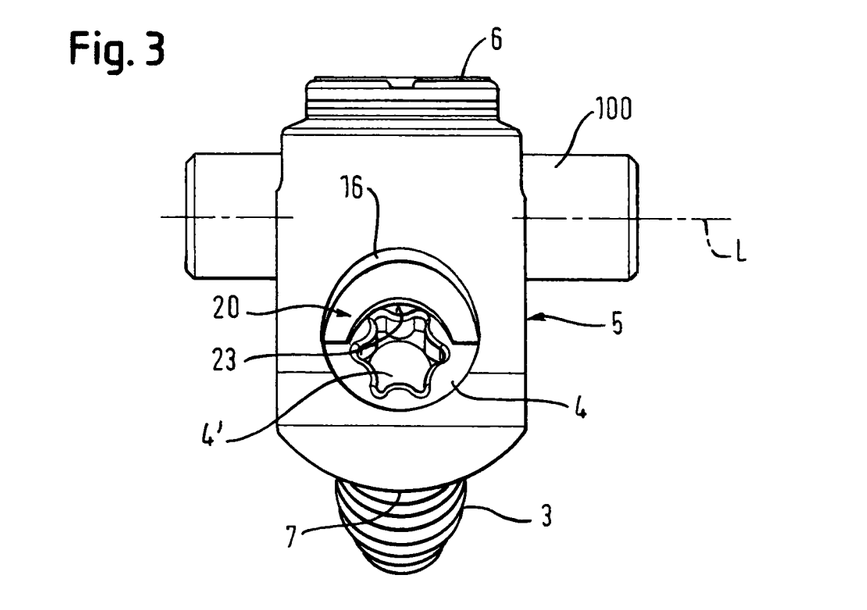
FIG. 3 shows a side view of the bone anchoring device of FIG. 1 in an assembled state.

The bone anchoring device 1 according to a first embodiment shown in FIGS. 1 to 3 comprises a screw member 2 having a threaded shaft 3 and a head 4 which is preferably shaped as a spherical segment, and a receiving part 5 for receiving a rod 100 to be connected with the screw member 2. The head 4 has a recess 4' at its free end for engagement with a screwing-in tool. The receiving part 5 has a first end 6 and an opposite second end 7 and first bore 8 being open to the first end 6 and defining a first bore axis 9. The receiving part 5 further has a substantially U-shaped recess 10 defining two free legs for receiving the rod 100 in-between. An internal thread 11 is provided at the legs.

The receiving part 5 further comprises a second bore 12 having a second bore axis 13, the second bore 12 being in communication with the first bore 8 and being open to a lateral side of the receiving part 5 between the first end 6 and the second end 7. The second bore axis 13 intersects the first bore axis 9 at an angle α of approximately 90°±12°, preferably slightly less than 90°, for example, 85°. The angle α is measured from the bottom of the receiving part 5. The diameter of the second bore 12 is smaller than the largest diameter of the head 4 but larger than the diameter of the threaded shaft 3 of the screw member 2. Adjacent to the outer wall of the receiving part 5 the second bore 12 comprises a section 14 with an increasing diameter in the direction of the outer wall. The diameter may increase, for example, in the shape of a conical section widening towards the outer wall. At the bottom of the receiving part 5 at the second end 7 a seat 15 is provided in which a part of the head 4 can rest. Preferably, the seat 15 has a spherical shape which is adapted to the spherical outer surface of the head 4.

Furthermore, the receiving part 5 comprises a third bore 16 having a third bore axis 17, the third bore 16 being in communication with the first bore 8 and being open to the lateral side of the receiving part 5 between the first end 6 and the second end 7 which is opposite to the second bore 12. Preferably, the third bore axis 17 is coaxial with the second bore axis 13 of the second bore 12. The diameter of the third bore 17 is larger than the largest diameter of the head 4 and thus larger than the diameter of the threaded shaft 3. Since the third bore 16 is in communication with the first bore 8 it is also in communication with the second bore 12.

The bone anchoring device 1 further comprises a pressure element 20 which has a substantially cylindrical outer surface with a largest diameter which is smaller than the inner diameter of the first bore 8 to such an extent that the pressure element 20 can move within the first bore 8. On its side facing the first end 7 the pressure element 20 comprises a spherical recess 21 the shape of which is adapted to the spherical surface of the head 4. On its opposite side the pressure element 20 comprises a cylindrical recess shaped and sized to receive a part of the rod 100 when the rod 100 is inserted. Further, the pressure element 20 comprises, on opposite sides of the cylinder axis of the cylindrical recess 22 at the end which has the spherical recess 22, cut-outs 23 for allowing a pivoting of the threaded shaft 3 when the head 4 of the screw member 2 is partly encompassed by the pressure element 20. As can be seen in FIG. 3 the cut-outs 23 have such a size so as to allow access to the recess 4' of the head 4 of the screw member 2 even if the bone anchoring device 1 is in an assembled state.

The bone anchoring device 1 also comprises a locking screw 25 with an external thread cooperating with the internal thread 11 of the receiving part 5.

The dimension of the pressure element 20 is such that in an assembled state when the screw member 2 is inserted into the receiving part 5 and the rod 100 is inserted into the pressure element 20 and when the locking screw 25 is not yet tightened, the bottom of the cylindrical recess 22 of the pressure element 20 projects above the bottom of the U-shaped recess of the receiving part 5.

The bone anchoring device 1 is assembled by first introducing the threaded shaft 3 through the third bore 16 and the second bore 12 which is in communication with the third bore 16 until the head 4 rests in the seat 15. Then the pressure element 20 is moved so as to engage the part of the spherical segment head 4 with its spherical recess 21. The bone anchoring device 1 may be preassembled in such a manner before it is used in surgery.

In use, first, the screw member 2, which is preassembled with the receiving part 5 and the pressure element 20, is screwed into the bone by engaging the recess 4' of the head 4 with a screwing-in tool reaching through the third bore 16. The first bore axis 9 encloses with the longitudinal axis of the screw member 2 an angle which can be approximately at least α±10° which depends on the size of the diameter of the second bore 12 and the size of the section 14 having the increasing diameter. Similarly, the longitudinal axis of the screw member 2 can include an angle of ±10° with an axis which is perpendicular to the first bore axis 9 and perpendicular to the longitudinal axis L of the rod 100. Hence, the screw member 2 can be pivoted in an angular range of ±10° within a cone around the second bore axis 13, the angular range depending on the size of the second bore 12 and of the section 14.

Once the rod 100 is inserted and the angular position between the screw member 2 and the receiving part 5 adjusted, the locking screw 25 is screwed-in which presses onto the rod 100 to fix the rod 100 and simultaneously presses onto the pressure member 20 via the rod 100 to lock the head 4 of the screw 2 in its position.

Figure 4:
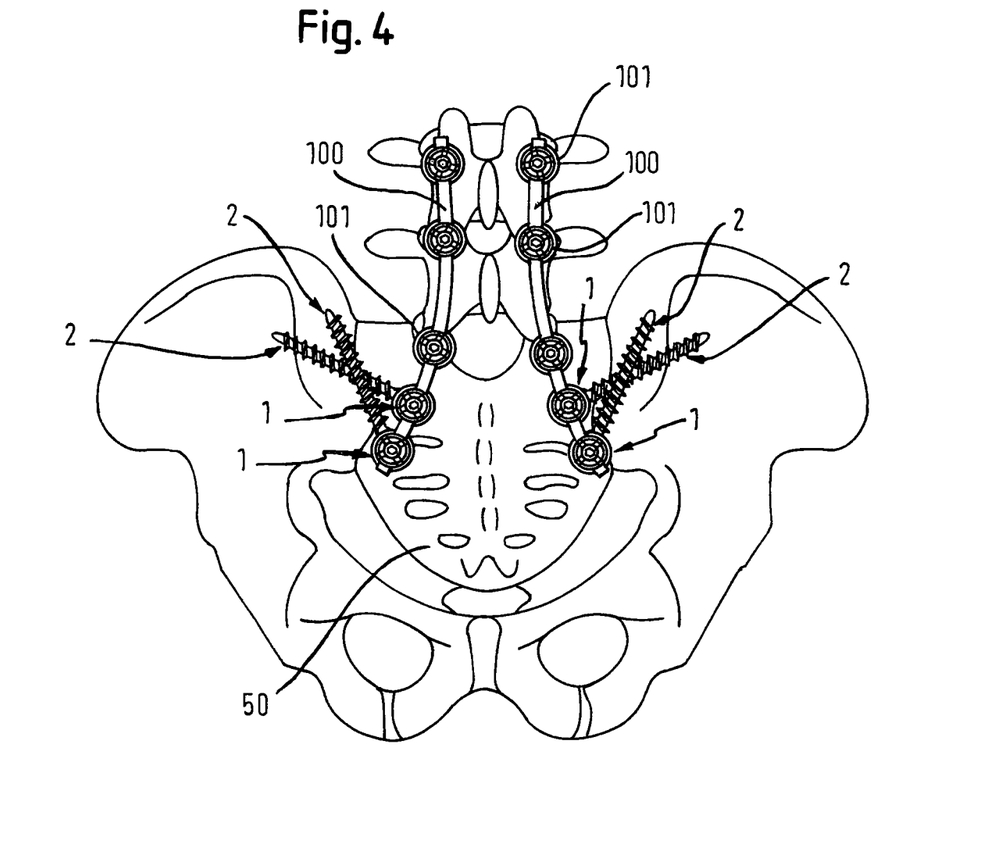
FIG. 4 shows a top view of a spinal stabilization system which includes the bone anchoring device according to the invention.

FIG. 4 shows the application of the bone anchoring device 1 in a stabilization system in the sacro-iliac region of the spine. A plurality of known anchoring devices 101 are each connected with a rod 100. The rods 100 of the stabilization system extend into the region of the sacrum 50. Bone anchoring devices 1 according to the invention are used for sacro-iliac fixation. For this purpose, it is necessary that the screw members 2 extend at an angle of approximately 90° from the plane which comprises the longitudinal rod axis L and the first bore axis 9. The screw member 2 can pivot with respect to the second bore axis within an angular range of ±10° as described above.

FIG. 5 to 8 show a second embodiment of the bone anchoring device. The bone anchoring device of the second embodiment differs from the bone anchoring device of the first embodiment in the construction of the second and third bore of the receiving part. All other parts are identical to the first embodiment and have the same reference numerals as in the first embodiment. A description thereof is not repeated. The receiving part 500 comprises a second bore 120 which is in communication with the first bore 8 and which defines a second bore axis 130. As in the first embodiment the second bore 120 is open to the lateral side of the receiving part 500 and the second bore axis 130 extends at an angle of approximately 90° from the plane defined by the longitudinal axis of the rod 100 and the first bore axis 9. The diameter of the second bore 120 is larger than the largest diameter of the head 4 of the screw member 2 such that the head 4 of the screw member 2 can be introduced into the receiving part 500 through the second bore 120 until the head 4 rests in the seat 15 on the bottom of the receiving part 500. On the side opposite to the second bore 120 a third bore 160 is provided which is in communication with the first bore 8 and which defines a third bore axis 170. The third bore axis 170 is preferably coaxial with the second bore axis 130. The third bore 160 is open to the lateral side and has a diameter which is at least as large so that a screwing-in tool can be introduced for engagement with the recess 4' of the head 4 but the diameter is smaller than the largest diameter of the head 4 so that the screw member 2 can not escape through the third bore 160. Since the third bore 160 is in communication with the first bore 8 it is also in communication with the second bore 120.

Figure 6A:
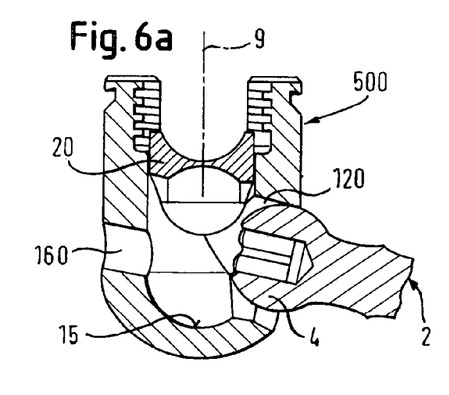
FIGS. 6a to 6c show cross-sectional views of different steps of assembly of the bone anchoring device according to FIG. 5.
Figure 6B:
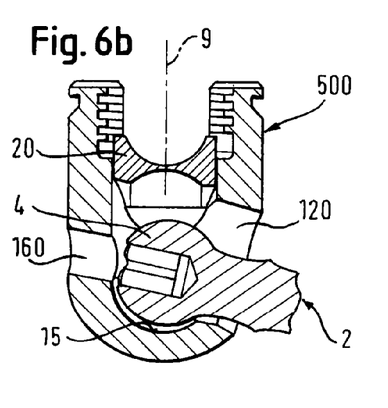
Figure 6C:
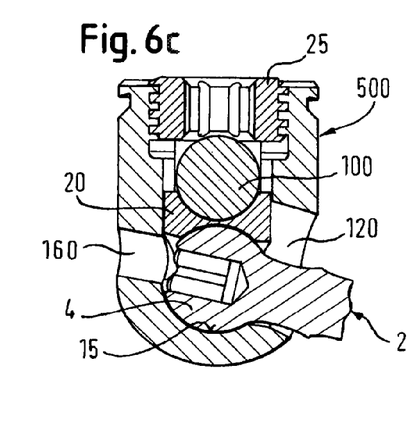
Figure 7:
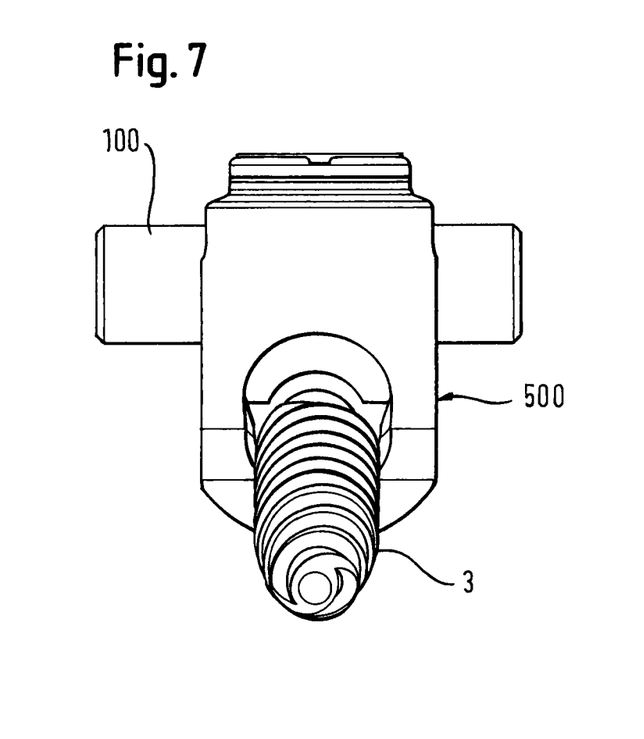
FIG. 7 shows a side view of the bone anchoring device according to FIG. 5 in an assembled state.
Figure 8:
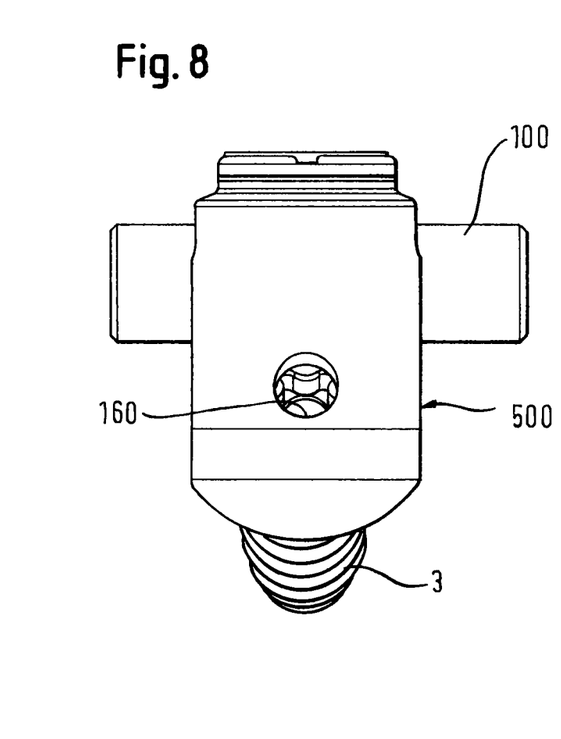
FIG. 8 shows a side view rotated by 180° of the bone anchoring device according to FIG. 5 in an assemble state.

The bone anchoring device 1 is preassembled as shown in FIGS. 6a and 6b in that the screw member 2 is introduced with its head 4 through the second bore 120 until the head 4 rests in the seat 15. Then, in use, the screw member 2 is screwed into the bone by introducing a screwing-in tool which engages the recess 4' of the head through the third bore 160. Thereafter, the angular position of the screw member 2 relative to the receiving part 500 is adjusted, the rod is inserted and the device is locked by screwing-in the screw 25.

Figure 5:
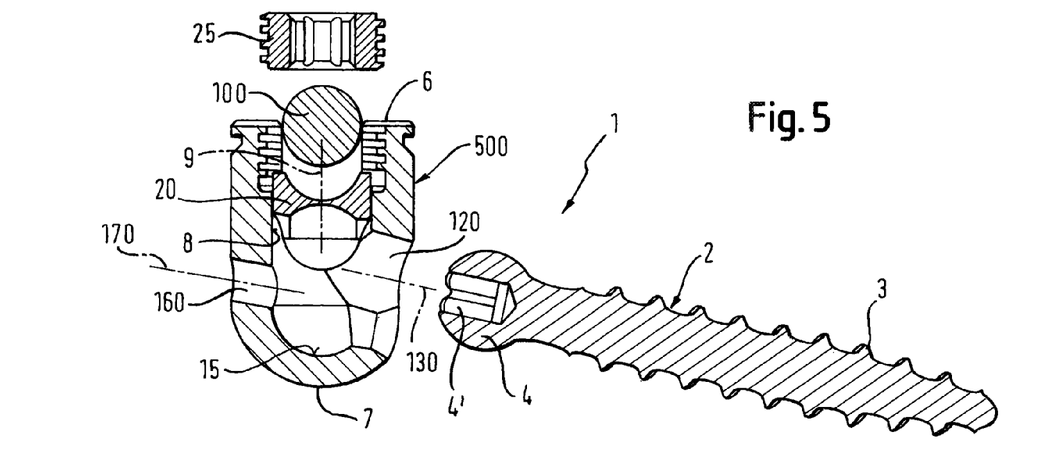
FIG. 5 shows an exploded cross-sectional view of the bone anchoring device according to a second embodiment.

In an alternative use, the screw member 2 can be screwed into the bone and the receiving part 500 can be later on connected to the screw member 2 by introducing the head of the screw member through the second bore 120 into the receiving part 500.

Figure 9:
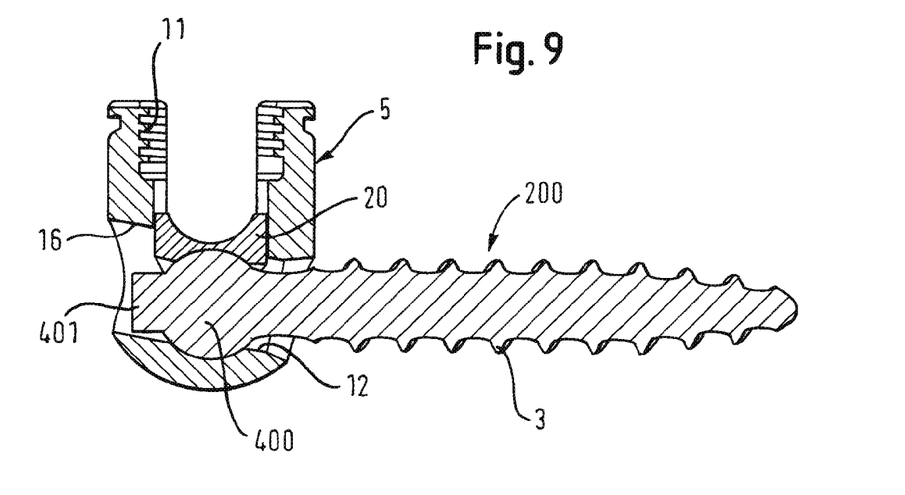
FIG. 9 is a sectional view of a bone anchoring device according to a third embodiment.
Figure 10:
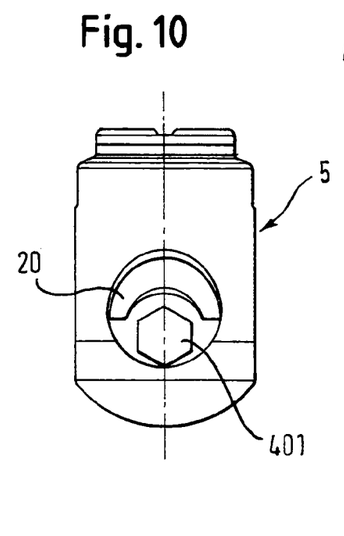
FIG. 10 is a rear side view showing the bone anchoring device of the third embodiment.
Figure 11:
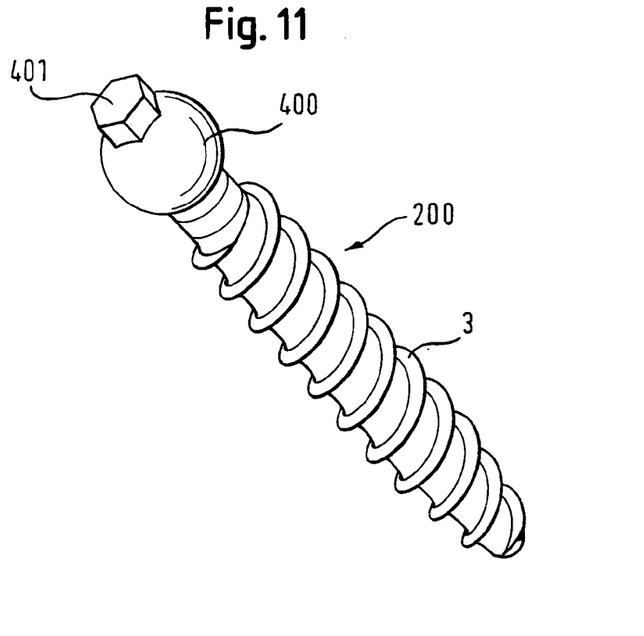
FIG. 11 is a perspective view of the bone anchoring element of the third embodiment.

FIGS. 9 to 11 show a bone anchoring device according to a third embodiment. The bone anchoring device differs from the bone anchoring device according to the first embodiment only in the design of the bone anchoring element. The receiving part 5 is identical. The bone anchoring element 200 comprises a threaded shaft 3 and a head 400. On its side opposite to the threaded shaft 3 the head 400 comprises a hexagonally-shaped projection 401 for engagement with a tool which can be introduced through the third bore 16. This has the advantage that the head 400 can be made as a solid sphere or spherical segment without a recess. The projection 401 can have any shape which is appropriate for engagement with a tool. In a further modification the projection 401 itself has a recess for engagements with a tool.

Modifications of the invention are possible, for example, in the case of the second embodiment when the screw member 2 is screwed-in into the bone first, and thereafter connected to the receiving part 500, it may be possible to omit the third bore 160. The size of the second bore may vary in order to allow pivoting of the bone screw member relative to the receiving part in an enlarged or in a reduced angular range. The cut outs 23 at the pressure element may be omitted, as long as it is possible to access the screw head with a tool. Alternatively, only one cut out is provided.

For the purpose of preassembly, it is possible to connect the pressure element 20 with the receiving part via crimp bores.

The seat 15 needs not to have a spherical shape, it can have another shape or be flat. For the closure mechanism other mechanisms than those using a single locking screw are possible. For example, a locking assembly consisting of a rod locking screw and a head locking nut-like element are possible. A pressure element in this case has upstanding legs projecting above the rod so that the pressure element can be pressed down independently of the rod.

The shaft need not to be threaded but can have any other shape and structure which allows retention in the bone. The pressure element can also be shaped as a flat disc.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring device comprising:
   a bone anchoring element having a shaft to be anchored in a bone and a head having a spherical surface portion;
   a receiving part for receiving a rod to be connected to the bone anchoring element, the rod having a longitudinal axis, the receiving part being formed in one piece and comprising:
      a first bore extending from a first open end to a second end along a first bore axis;
      two legs having first free ends at the first open end of the bore and extending from the first free ends in a direction of the first bore axis to second ends of the legs wherein the legs are joined to define a U-shaped recess shaped and sized to receive the rod;
      a second bore having a second bore axis, the second bore being in communication with the first bore and being sized to receive the head with a part of the shaft extending through the second bore; wherein the second bore is configured to block the shaft of the bone anchoring element, when the bone anchoring element is seated within the receiving part, from moving to a position wherein a longitudinal axis of the shaft is aligned with the first bore axis;
      wherein an angle between the second bore axis and a plane defined by the first bore axis and the longitudinal axis of the rod is approximately 90°; and
   a pressure member acting onto the head to lock the position of the head relative to the receiving part.

2. The bone anchoring device according to claim 1, wherein the first bore axis and the second bore axis intersect each other.

3. The bone anchoring device according to claim 1, wherein pivoting of the bone anchoring element is allowed when the bone anchoring element is seated within the receiving part.

4. The bone anchoring device according to claim 1, wherein the second bore comprises a section with a diameter increasing toward the outer wall of the receiving part to allow pivoting of the bone anchoring element when the bone anchoring element is seated within the receiving part.

5. The bone anchoring device according to claim 1, wherein the receiving part comprises a third bore having a third bore axis, the third bore being in communication with the second bore and arranged on the side of the receiving part which is opposite to the second bore.

6. The bone anchoring device according to claim 5, wherein the second bore axis and the third bore axis are substantially coaxial.

7. The bone anchoring device according to claim 5, wherein the diameter of the third bore is larger than the largest diameter of the head.

8. The bone anchoring device according to claim 5, wherein the diameter of the third bore is smaller than the largest diameter of the head.

9. The bone anchoring device according to claim 1, wherein the diameter of the second bore is smaller than the largest diameter of the head.

10. The bone anchoring device according to claim 1, wherein the diameter of the second bore is larger than the largest diameter of the head.

11. The bone anchoring device according to claim 1, wherein the angle between the second bore axis and the plane is 90°±12°.

12. The bone anchoring device according to claim 1, wherein the bone anchoring element is pivotable when seated within the receiving part in an angle of 10° relative to the second bore axis.

13. The bone anchoring device according to claim 1, wherein the receiving part comprises a seat for the head, the seat being part of a surface of the second bore.

14. The bone anchoring device according to claim 1, wherein the seat has a spherical surface portion which corresponds to the spherical surface portion of the head.

15. The bone anchoring device according to claim 1, wherein the pressure member has the spherical surface portion which corresponds to a spherical surface of the head.

16. The bone anchoring device according to claim 1, wherein the head comprises a projection at its end opposite to the shaft for engagement with a tool.

17. A method of using a bone anchoring device, the bone anchoring device comprising a bone anchoring element having a shaft to be anchored in a bone and a head having a spherical surface portion, a receiving part for receiving a rod to be connected to the bone anchoring element, the rod having a longitudinal axis, the receiving part being formed in one piece and comprising a first bore extending from a first open end to a second end along a first bore axis, two legs having first free ends at the first open end of the bore and extending from the first free ends in a direction of the first bore axis to second ends of the legs wherein the legs are joined to define a U-shaped recess shaped and sized to receive the rod, a second bore having a second bore axis, the second bore being in communication with the first bore and being sized to receive the head with a part of the shaft extending through the second bore, wherein the second bore is configured to block the shaft of the bone anchoring element, when the bone anchoring element is seated within the receiving part, from moving to a position wherein a longitudinal axis of the shaft is aligned with the first bore axis, wherein an angle between the second bore axis and a plane defined by the first bore axis and the longitudinal axis of the rod is approximately 90°, and a pressure member, the method comprising:

inserting the bone anchoring element in the receiving part; and inserting the pressure member in the receiving part, the pressure member configured to act on the head to lock the position of the bone anchoring element relative to the receiving part.

18. The method according to claim 17, wherein inserting the bone anchoring element comprises inserting the head first from outside the receiving part through the second bore.

19. The method according to claim 17, wherein inserting the bone anchoring element comprises inserting the shaft first from outside the receiving part through a third bore of the receiving part, the shaft at least partly extending through the second bore such that the head is inserted in the receiving part from outside the receiving part through the third bore, the third bore being on an opposite side of the receiving part relative to the second bore.

20. The method according to claim 17, further comprising screwing the shaft into a bone with a tool inserted into a third bore of the receiving part being on an opposite side of the receiving part relative to the second bore, the tool engaging a portion of the head.

\* \* \* \* \*

UNITED STATES PATENT AND TRADEMARK OFFICE
CERTIFICATE OF CORRECTION

PATENT NO. : 8,641,737 B2  Page 1 of 1
APPLICATION NO. : 11/697220
DATED : February 4, 2014
INVENTOR(S) : Wilfried Matthis et al.

It is certified that error appears in the above-identified patent and that said Letters Patent is hereby corrected as shown below:

In the Specification

Column 1, line 60          Delete "and"

Insert -- an --

Column 2, line 44          Delete "assemble"

Insert -- assembled --

In the Claims

Column 6, Claim 1, line 9  Delete "alianed"

Insert -- aligned --

Signed and Sealed this
Thirteenth Day of January, 2015

Michelle K. Lee
*Deputy Director of the United States Patent and Trademark Office*